United States Patent [19]

North, Jr. et al.

[11] Patent Number: 5,395,588
[45] Date of Patent: Mar. 7, 1995

[54] CONTROL OF FLOW CYTOMETER HAVING VACUUM FLUIDICS

[75] Inventors: Howard North, Jr.; Kenneth F. Uffenheimer, both of Los Gatos, Calif.

[73] Assignee: Becton Dickinson and Company, Franklin Lakes, N.J.

[21] Appl. No.: 19,716

[22] Filed: Feb. 19, 1993

Related U.S. Application Data

[63] Continuation-in-part of Ser. No. 989,622, Dec. 14, 1992, abandoned.

[51] Int. Cl.⁶ .................... G01N 21/11; G01N 27/08
[52] U.S. Cl. ........................................ 422/81; 422/67; 422/68.1; 73/864.83; 436/63
[58] Field of Search .............. 422/68.1, 81, 63, 67; 73/864.83; 436/63

[56] References Cited

U.S. PATENT DOCUMENTS

| | | | |
|---|---|---|---|
| 2,656,508 | 10/1953 | Coulter . | |
| 2,869,078 | 1/1959 | Coulter et al. . | |
| 3,793,589 | 2/1974 | Puckette | 325/137 |
| 3,810,010 | 5/1974 | Thom | 324/71 CP |
| 3,960,020 | 6/1976 | Gordon et al. | 73/423 A |
| 4,175,662 | 11/1979 | Zold | 209/552 |
| 4,198,160 | 4/1980 | Kachel et al. | 356/72 |
| 4,230,558 | 10/1980 | Fulwyler | 209/3.1 |
| 4,318,885 | 3/1982 | Suzuki et al. | 422/68 |
| 4,478,095 | 10/1984 | Bradley et al. | 422/67 |
| 4,673,288 | 6/1987 | Thomas et al. | 356/72 |
| 4,713,974 | 12/1987 | Stone | 422/67 |
| 4,756,427 | 7/1988 | Gohde et al. | 209/3.1 |
| 4,844,610 | 7/1989 | North | 356/73 |
| 5,030,002 | 7/1991 | North | 356/73 |
| 5,040,890 | 8/1991 | North | 356/72 |

FOREIGN PATENT DOCUMENTS

| | | |
|---|---|---|
| 0068404 | 1/1983 | European Pat. Off. . |
| 0478392A3 | 4/1992 | European Pat. Off. . |
| 04036636 | 2/1992 | Japan . |

OTHER PUBLICATIONS

Perry et al. "Membrane Processes" in Chemical Engineer's Handbook, McGraw Hill, N.Y. pp. 17-34 to 17-43.
Principles of Flow Cytometry—J. L. Haynes—Cytometry Supplement 3:7-17 (1988) pp. 7-17.

*Primary Examiner*—James C. Housel
*Assistant Examiner*—Jan M. Ludlow
*Attorney, Agent, or Firm*—Allen W. Wark

[57] ABSTRACT

The present invention relates to a system for controlling the movement or transport of objects such as cells and other particles in a moving liquid stream. More particularly the invention relates to a system including a vacuum pump which pulls the sheath fluid from an open supply reservoir through a flow cell assembly where cell analysis occurs and discharges the flow cell effluent to an open waste reservoir. A pressure drop is created through the conduit leading from the supply reservoir to the flow cell which aspirates the cell suspension from an open sample vessel into and through the flow cell. The vacuum is regulated by controlling the electric power applied to the vacuum pump motor. Starting, stopping, reverse flushing, and draining of the flow cell assembly are controlled by programming the operation of four electric solenoid valves in fluid communication with the flow cell inlet and outlet passages, the operation of a reverse flush pump and, the operation of an electrically controlled tube lifter. A deaerator is provided to remove some of the air dissolved in the sheath fluid provided to the flow cell assembly to prevent the release of air and formation of adherent air bubbles in sensitive areas of the flow cell assembly.

11 Claims, 6 Drawing Sheets

A
CONTROL OF FLOW CYTOMETER HAVING VACUUM FLUIDICS

This is a continuation-in-part of Ser. No. 07/989,622, filed Dec. 14, 1992, now abandoned.

FIELD OF THE INVENTION

The present invention relates to a system for controlling a flow cytometry process in which cells and other particles suspended in a moving liquid stream, or sheath fluid, are measured and/or separated. More particularly the invention relates to a flow cytometer control system driven by a vacuum pump in which the starting, stopping and draining of the flow cell is controlled by programming the operation of four solenoid-actuated valves connected to the inlet and outlet conduits of the flow cell and the operation of an electrically controlled cell sample tube lifter and operation of pressure pump which back flushes the sample introduction conduit. A flow restrictor creates a pressure drop in the sheath fluid flow between the supply reservoir and the flow cell developing a vacuum which aspirates cell sample from an open cuvette or tube into and through the flow cell.

BACKGROUND ART

Flow cytometry, the measurement of cells in a moving liquid stream, is a valuable analysis tool in research laboratories. Conventional flow cytometry devices for sorting objects such as cells and particles basically consist of a liquid stream forming a sheath fluid into which cell sample is introduced then focused through an orifice. As the objects pass through the orifice, particular characteristics of the objects are determined based upon the analyzing or counting capabilities of the device. Usually, the device can sort or count at high speeds, collecting tens of thousands of the objects based on a variety of chemical and physical characteristics such as size, granulation of the cytoplasm and presentation of specific antigens. Accordingly, there has been considerable interest in flow cytometry to sort objects for subsequent analysis.

One commercially available flow cytometer which relies on a hydrodynamically focused fluid system is known as the FACScan TM instrument sold by Becton Dickinson Immunocytometry Systems, San Jose, Calif. The FACScan TM instrument rapidly analyzes cells on the basis of fluorescence and light scatter properties. Analysis is accomplished by introducing cells in a suspension to the center of a focused liquid stream thus causing them to pass, one at a time, through a focused light from a high powered laser. Each cell is individually characterized by its light scatter signals and by the intensity and color of fluorescence emitted while it is illuminated. This system is described in U.S. Pat. No. 4,844,610 issued Jul. 4, 1989 to North, U.S. Pat. No. 5,030,022 issued Jul. 9, 1991 to North and U.S. Pat. No. 5,040,890 issued Aug. 20, 1991 to North.

Typically flow cytometers systems have been implemented as pressure driven fluidics systems driven by pressure pumps. However, pressure driven systems have proven disadvantageous in that system leaks produce sprays of sheath fluid which may expose the operator to bio-hazardous substances and cause damage to optical and electronic components of the instrument. Regulatory valves required to control pressure driven cytometry systems tend to become clogged with blood cells causing the valves to stick or otherwise malfunction. In addition, the design of pressure driven fluidics systems is more complicated than is the design of vacuum driven fluidics systems since pressure driven systems require the use of pressurized connections for the supply reservoir and for other features necessary for the system to withstand high system pressure levels. Pressure driven systems also require the sample vessel to sealably engage the flow cell assembly. Removal of the sample vessel can produce hazardous aerosols and back flow dripping of bio-hazardous fluids.

Thus, a vacuum driven flow cytometry system provides many advantages over a pressure driven system. The design of the supply reservoir is greatly simplified, not requiring the use of pressurizing connections, and can be refilled by gravity drain from a elevated supply vessel. In addition, there is no back-flow drip from the cell sample uptake tube, used to introduce the cell sample into the sheath fluid flow, which may expose the operator to bio-hazardous substances. Cell sample vessels do not have to be pressurized or sealably engage the instrument to contain the system fluid allowing a new freedom of design in terms of the size and shape of the cell sample vessel. This freedom of design facilitates the design of auxiliary equipment, such as automatic tube lifters, which improve cell sample presentation. Another advantage realized is that the descent of the tube lifter can be prolonged allowing fluid residue from the sample uptake tube to drain into the cell sample vessel thus minimizing cell sample carryover which could skew test results of subsequent test runs. Finally, use of vacuum driven fluidics provides the opportunity to design a system in which the pump is utilized on a "demand" basis, being turned off once the system has reached a predetermined system vacuum or pressure level thus increasing the service life of the pump.

A major problem encountered in the development of a vacuum driven flow cytometer is the creation of air bubbles in the sheath fluid as the system pressure level is reduced to a level below atmospheric pressure. Air dissolved in the sheath fluid at atmospheric pressure comes out of solution when the sheath fluid is subjected to a vacuum. The bubbles lodge in troublesome areas such as in the analysis region of the flow cell. The bubbles may deflect cells from their proper trajectory through the illuminated area or analysis region of the flow cell. The present invention solves this problem through the use of a deaerator connected to the intake passage of the flow cell which removes much of the air dissolved in the sheath fluid.

Another problem presented in the development of a vacuum driven flow cytometer is air being drawn into the flow cell by the residual vacuum remaining in the flow cell at the end of the test cycle. Thus, a means is required to equalize the vacuum developed in the flow cell thereby preventing air from being drawn into the flow cell. This problem is solved by providing a valve, connected to an outlet passage of the flow cell, which vents the flow cell to atmospheric pressure as the tube lifter is descending thereby preventing air from being drawn into the flow cell. Computer control of valve actuation and the rate of descent of the tube lifter allows synchronous programmed control of the timing of these components. A rate of tube lifter descent which is sufficiently slow to permit the flow cell to fully vent before the uptake tube is removed from the analysis region is specified in programmed control.

SUMMARY OF THE INVENTION

It is therefore an object of the present invention to provide a system architecture and related method for control of a flow cytometer process having vacuum fluidics. The present invention provides many advantages over existing cytometers which use pressure driven fluidics and valves to regulate sheath and sample flow and which typically have manual sample presentation.

Thus according to one aspect of the present invention, a flow cytometer control system is described which includes a flow cell with intake and outlet passages, a vacuum pump for drawing the sheath fluid through the flow cell and a flow restrictor, connected to the intake passage, for developing a pressure drop proximate to the cell sample vessel which aspirates cell sample from the vessel into the flow cell.

According to another aspect of the present invention, a flow cytometer control system is described which includes a first valve V1 connected to the intake passage and second valve V2 connected to an outlet passage wherein opening valve V2 a predetermined time $T_1$ before opening valve V1 allows cell sample to be pulled through the flow cell for a brief period with full system vacuum before the sheath fluid flow is begun thereby "boosting" the cell sample concentration through the orifice or cell analysis portion of the flow cell to the normal sample flow rate more rapidly.

According to another aspect of the present invention, a control system is described which includes a vacuum sensor connected to an outlet of the flow cell for sensing the pressure or vacuum level of the sheath fluid and a driver for regulating power delivered to the vacuum pump motor. A solid state circuit, coupled to the vacuum sensor and the motor driver, is provided for controlling the operation of the motor driver based on the system vacuum level at the outlet of the flow cell. Power delivered to the vacuum pump motor is modulated to adjust the vacuum level to a predetermined fixed value.

According to another aspect of the present invention, a control system is described for a vacuum driven system which includes a deaerator for removing gas dissolved in the sheath fluid which is released by the lower pressure level of the vacuum drive.

According to another aspect of the present invention, a processor controlled automatic tube lifter is described which permits a slow rate of tube descent allowing the external residue on the sample uptake tube to drain into the cell sample vessel thereby reducing carryover of cell sample between test cycles.

According to another aspect of the present invention, a control system is described which includes a third valve V3 for venting the flow cell to atmospheric pressure as the tube lifter descends thereby equalizing the vacuum developed in the flow cell to prevent air from being drawn into the flow cell through the sample injection tube.

According to another aspect of the present invention, a method for controlling a cytometer system is described which includes the steps of providing a flow cell which is connected to a sheath fluid system and driven by a vacuum pump, aspirating the cell sample into the flow cell for a predetermined time $T_1$ to boost the cell sample flow rate through the flow cell, then circulating sheath fluid through the flow cell for cell analysis. The additional step of reverse-flushing the flow cell to minimize carryover of residual cell sample and contaminants which could skew test results is also described. Control of the speed of tube lifter descent is provided for operator convenience, enhancing his ability to control the system in optimum fashion.

DETAILED DESCRIPTION OF THE PREFERRED EMBODIMENTS

Figure 1:
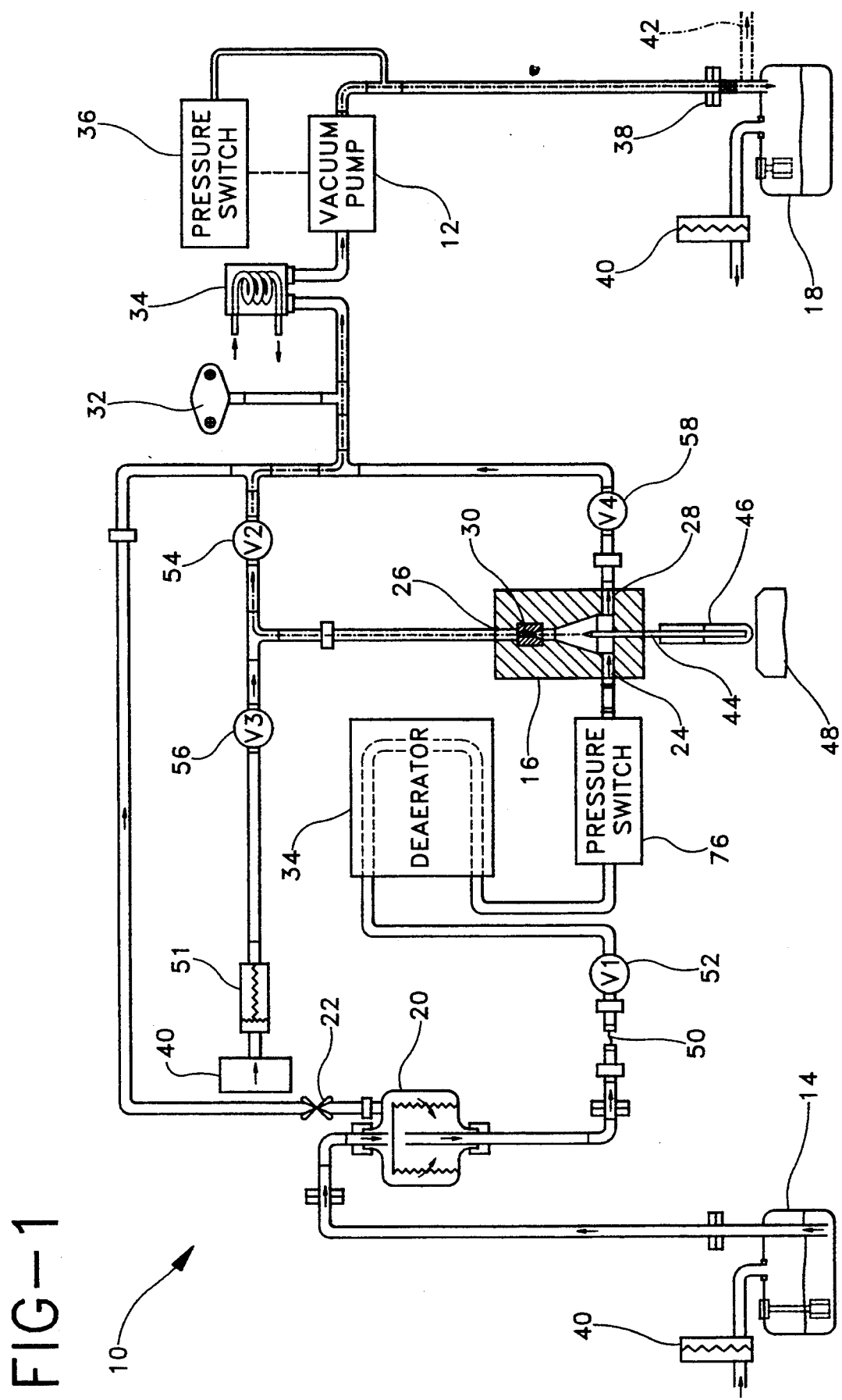
FIG. 1 is a schematic representation of the fluidics design of the present invention, the flow cytometer control system.

Referring now to the drawings wherein like reference numerals are used to reference identical components in various views, FIG. 1 is a schematic representation of the fluidics of the present invention, flow cytometer control system, generally denoted by the numeral 10. System pressure or vacuum is developed by a vacuum pump 12, which draws sheath fluid from a supply reservoir 14 through a flow cell assembly 16 where cell sample is introduced and cell analysis occurs. Waste effluent is then discharged into a waste reservoir 18. The sheath fluid from supply reservoir 4 is purified before entering flow cell assembly 16 by drawing it through a 0.45 micron saline filter 20. A manual tubing pinch valve 22, provided in an outlet passage of the saline filter 20, is opened to bleed off air trapped in the saline filter 20. A KNF Neuberger Pump Model NF30KVDC is selected for use as vacuum pump 12 because it is self priming and because an identical pump can be used as pressure pump 76 which drives the deaerator 34 thus minimizing the number of components needed in stock to manufacture the invention.

Flow cell assembly 16 includes an intake passage 24 and first and second outlet passages 26 and 28, respectively. Within the flow cell assembly 16, sheath fluid is focused through a cell analysis region 30. A test sample containing objects, usually tens of thousands of blood cells, is analyzed by counting or sorting the cells at high speeds based on a variety of chemical and physical characteristics such as size, granulation of the cytoplasm and the presence of specific antigens.

The vacuum level of the flow cytometer control system 10 is regulated to a fixed value by modulating the power delivered to the motor of the vacuum pump 12 based upon the system vacuum level sensed by a vacuum sensor 32 which is connected to the first and second outlet passages, 26 and 28, of the flow cell assembly 16. Pulsations in vacuum level are attenuated by a pulsation damper 34 which can be a jar with an internal volume many times (10 to 1000 times) the stroke volume of the vacuum pump which is preferably a piston type with inlet and outlet check valves. Normally closed vacuum pump discharge pressure switch 36, for example Air Logic Switch Model F4100-100-50W, is connected in series with the motor of vacuum pump 12 to prevent excessive pump discharge pressure which could cause leaks or damage to vacuum pump 12. Pressure switch 36 shuts off the vacuum pump 12 when the waste reservoir 18 is removed. The quick disconnect device 38 seals off the flow cytometer control system 10 when the waste reservoir 18 is removed. Vent filters 40, for example 0.2 micron TEFLON filters, are provided on the supply reservoir 14 and on the waste reservoir 18 to contain aerosols and prevent fluid spillage when the reservoirs 14 and 18 are handled outside of the instrument. A remote discharge connection 42 may replace the waste reservoir 18, eliminating the need for the operator to handle hazardous waste fluid containers.

Providing a flow cytometer system which is driven by a vacuum pump proves advantageous in that the sheath fluid supply reservoir 14 is not pressurized allowing a simple, inexpensive design without pressurized connections or other features which are required to provide a positive system pressure. The supply reservoir 14 can also be refilled by gravity drain from a superior supply vessel and waste sheath fluid may be discharged to a remotely located disposal site without affecting the operation of the system. The remote discharge feature eliminates the need for the operator to empty the waste reservoir 18 which may expose the operator to bio-hazardous material. In addition, system leaks do not produce sprays of sheath fluid which can damage optical, electronic, or other components of the test instrument.

The cell sample is drawn into the flow cell assembly 16 through a sample uptake tube 44. The cell sample vessel 46 is placed in a tube lifter 48 which is raised toward the flow cell assembly 16 until the sample uptake tube 44 is immersed in the sample contained within cell sample vessel 46. A flow resistor 50, which may comprise a piece of conduit of a fixed length with a reduced inside diameter or a needle valve, creates a pressure drop in the conduit leading to flow cell assembly 16 thereby developing a vacuum proximate to the flow cell assembly 16 which aspirates the sample from the cell sample vessel 46, usually an test tube or cuvette, into the flow cell assembly 16 at the proper rate. The use of vacuum driven fluidics proves advantageous in that dripping of the sheath fluid from the sample uptake tube 44 (which could produce bio-hazardous conditions) is avoided. Therefore, auxiliary devices to contain the drip from the sample uptake tube 44 after a test run are not required. In addition, cell sample vessels do not have to be pressurized or to sealably engage the flow cell assembly 16 thereby allowing freedom of design in terms of the size and shape of the cell sample vessel 46 and freedom of choice in terms of designing a means for cell sample presentation.

The deaerator 34 is length of thin walled silicone rubber tubing. The sheath fluid flows inside the tubing while the outside of the tubing is exposed to the full system vacuum level. Because silicone rubber is permeable to the passage of air, with its major components of oxygen and nitrogen, these gases diffuse through the silicone rubber tubing and are drawn off by the system vacuum. To construct the deaerator 34, a length of silicone rubber tubing is coiled up inside a 4 oz plastic jar. The system vacuum is applied to the jar interior which then also serves as the pulsation damper 34. The tubing is medical grade Dow Corning tubing with 0.132 inch inside diameter, 0.183 outside diameter and a length of 50 inches. Tested at a system vacuum of 0.3 of an atmosphere, this tubing has twice the needed capacity to deaerate the sheath fluid so that no bubbles are formed in the flow cell inlet regions.

The tube lifter 48 is a linear motion device which travels from a bottom position, where the cell sample vessel 46 is installed or removed conveniently by the operator, to an upward position over a distance of about five inches. In the upward position, the tube lifter 48 presents the cell sample vessel 46 to the sample uptake tube 44 through which the cell sample is aspirated from the cell sample vessel 46 into the flow cell assembly 16. The tube lifter 48 is guided on a rod during its linear travel and is driven upward and downward by a small DC motor operating through a gear train with a rack and pinion to produce the linear motion. Its extremes of travel are sensed by opto-interruptive devices which sense the interruption of an optical beam by a sheet metal flag on the carriage of the tube lifter 48 when the tube lifter 48 has traveled to the top or bottom position. These sensing devices are positioned at both the top and bottom positions which causes the power to the motor of tube lifter 48 to be shut off. The carriage of tube lifter 48 remains in the down position by gravity when no voltage is applied to the motor of tube lifter 48. The carriage of tube lifter 48 is held in the upward position by a retaining magnet.

Four normally-closed solenoid-actuated valves V1–V4, 52, 54, 56, 58 respectively, are connected to the flow cell assembly 16 to provide control of fluid flow. V1 is connected to the intake passage 24 of flow cell assembly 16. V2 54 is connected to the first outlet passage 26 of the flow cell assembly 16 and to the vacuum pump 12 providing communication between the flow cell assembly 16 and the waste reservoir 18. V3 56, also connected to the first outlet passage 26, vents to atmospheric pressure. V4 58, is connected to the second outlet passage 28 of flow cell assembly 16 providing a communication path through the flow cell assembly 16 to waste reservoir 18.

Figure 2:
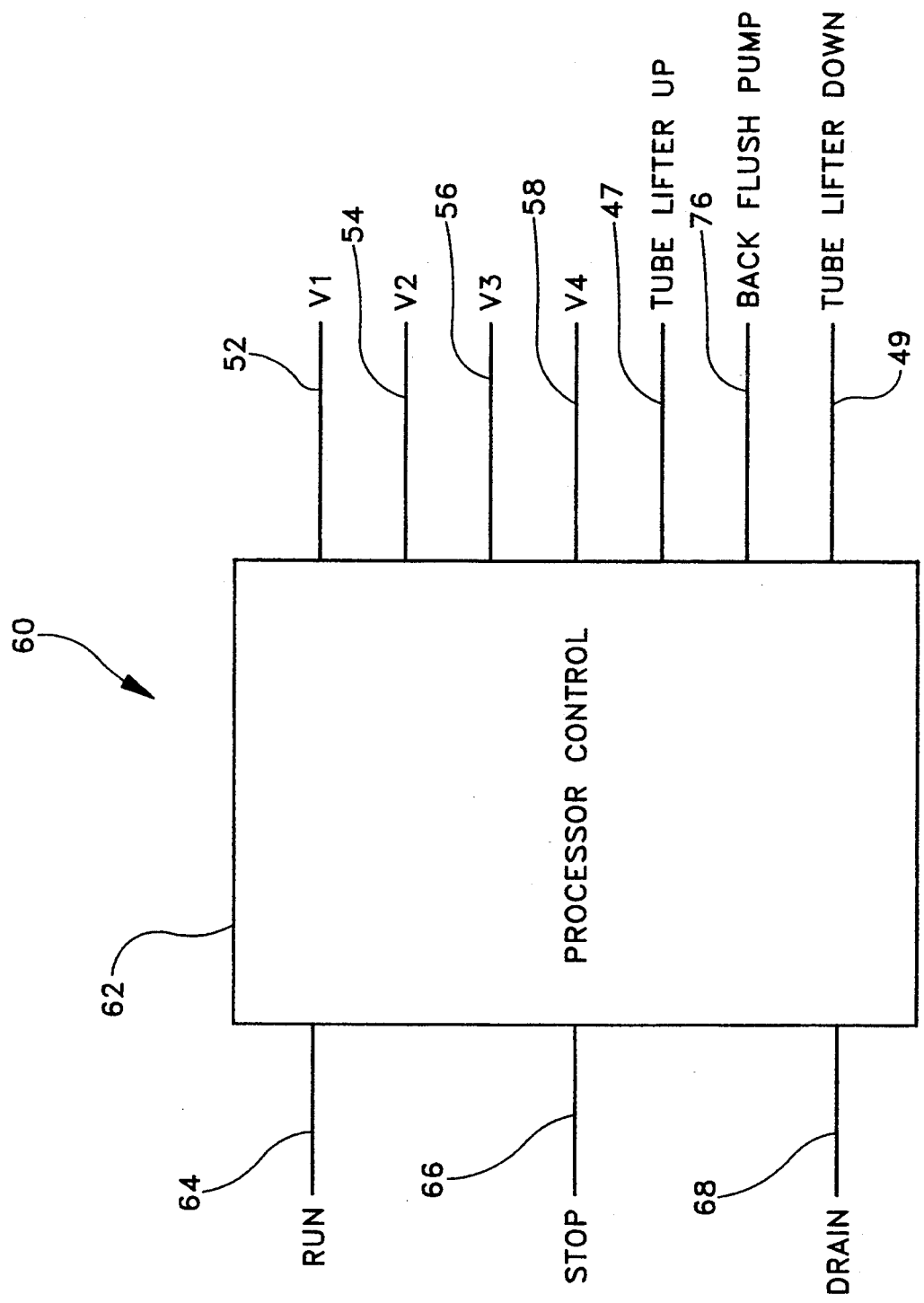
FIG. 2 is a block diagram of the computer control for the present invention.

FIG. 2 is a schematic representation of the computer control system for the flow cytometer control system. The computer control system 60 includes microprocessor unit 62 comprises a single circuit board mounted inside the instrument cabinet of the flow cytometer control system 10. Operator access switches 64–68 actuate RUN, STOP (STANDBY) and DRAIN test modes, respectively. The micro-processor unit 62, for example Intel 286, may also be used for automatic control. During STOP (STANDBY) mode, all the valves V1–V4 52, 54, 56, 58 are closed. During normal test RUN mode, V1 52 and V2 54 are open permitting sheath fluid to flow through the flow cell assembly 16. The sheath fluid is then discharged as effluent into waste reservoir 18. Valves V3 56 and V4 58 are opened by actuating the DRAIN operator access switch 68 to provide an alternative communication path through the cell analysis region 30 of the flow cell assembly 16 to waste reservoir 18. During DRAIN mode, the flow cell assembly 16 is drained to clear clogs and remove gas bubbles trapped in the flow cell assembly 16. Opening valves V3 56 and V4 58 allows air to enter the flow cell and fluid to exit through valve V4 58. An air flow restrictor 51 with a protective filter is provided between valve V3 56 and the atmospheric inlet to limit airflow during the DRAIN mode to a value less than the vacuum pump capacity so that the system vacuum or pressure level can be maintained.

Actuation of an operator access switches 64–68, designating RUN, STOP (STANDBY), and DRAIN modes respectively, by the operator causes the microprocessor unit 62 to output control signals which energize the appropriate combination of valves V1–V4 52–58 and which appropriately position the tube lifter 48 and which energize the reverse flush pump 76 to implement a desired test mode. Computer control allows valve actuation timing, tube lifter ascent and descent timing and reverse flush pump timing to be specified in computer programs which are downloaded into the micro-processor unit 62 from the storage medium 72. The storage medium 72 may be provided, for example, by a floppy disk inserted into a floppy disk drive 74 which is also contained in the computer control system 60. Programmed control of the solenoid-actuated valves V1–V4 52–58, the tube lifter 48 and the reverse flush pump 76 allows the designer to finely tune the component actuation timing to optimize the fluidics performance of the overall system thereby minimizing cell sample carryover, optimizing auto-boost of the cell sample flow rate and achieving stabilization of system vacuum level and fluid flow.

Figure 3A:
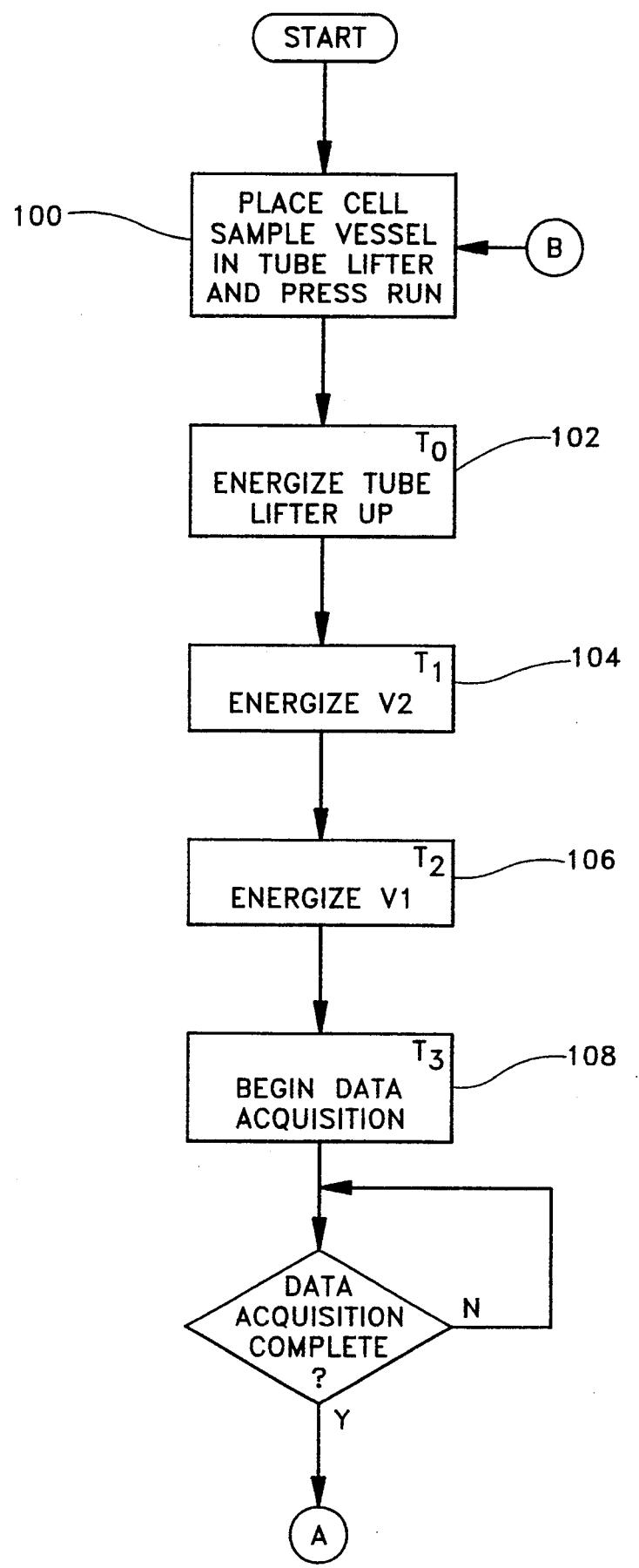
FIGS. 3A AND 3B are a logic flow diagram depicting method steps for the computer control of valves V1-V4, the reverse-flush pump, and the tube lifter.
Figure 3B:
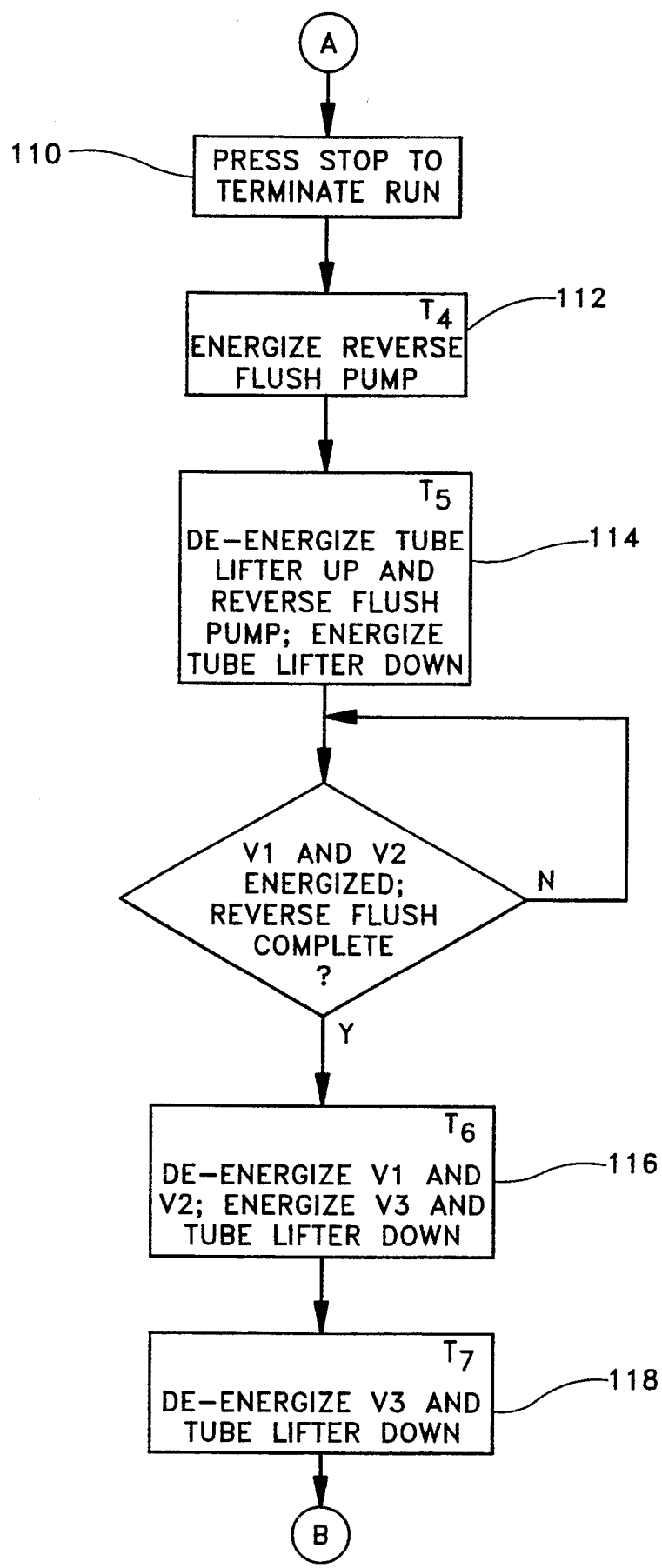
Figure 4:
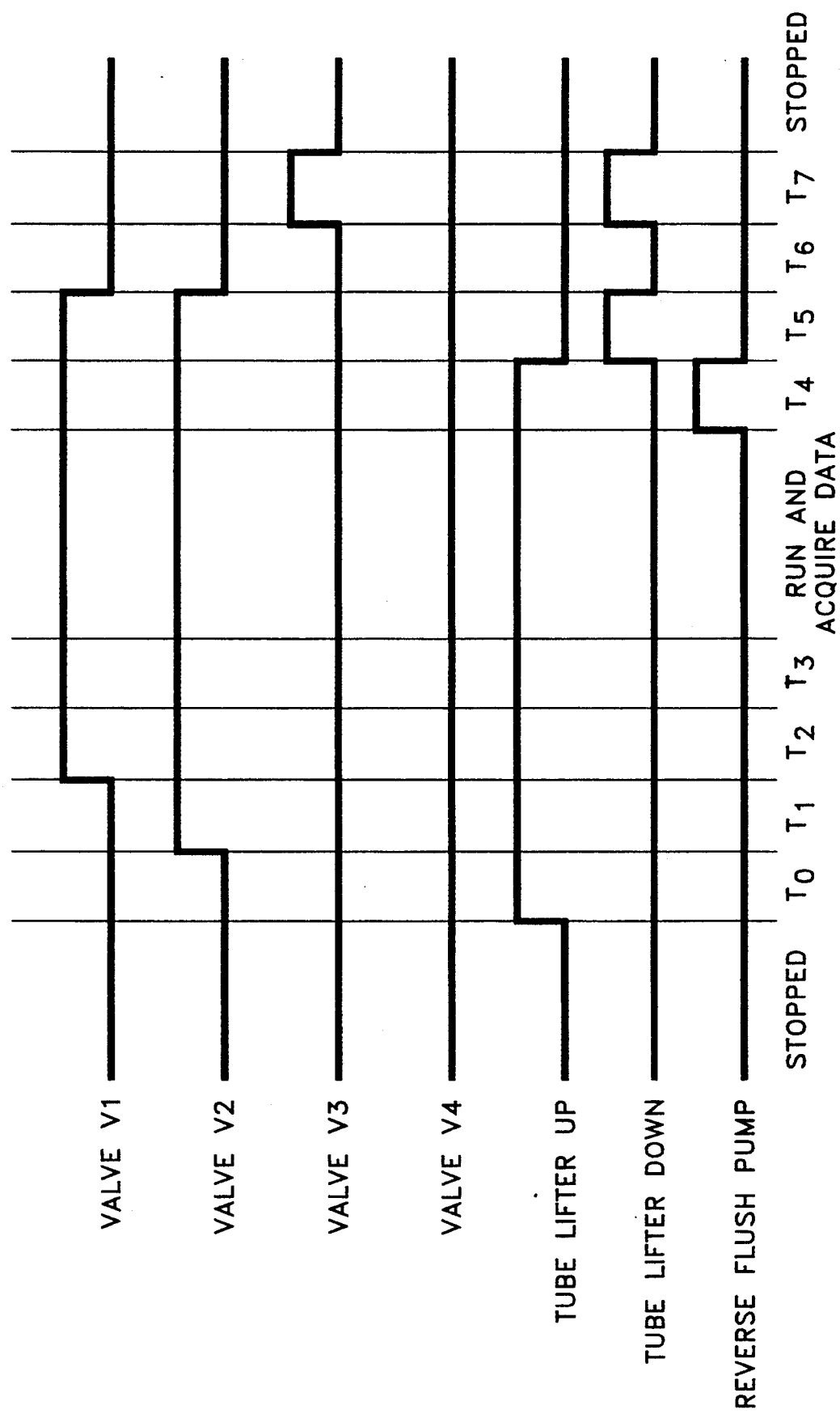
FIG. 4 is a timing diagram depicting the operation of valves V1-V4.

FIGS. 3A and 3B are a flow diagram depicting the method steps for computer program control of the present invention, the flow cytometer control system including valves V1–V4 52–58, the reverse or back-flush pressure pump 76, and the tube lifter 48. FIG. 4 is a timing diagram depicting the energized states of these components during normal test RUN cycle. As shown in FIG. 3A, the method of the present invention begins in step 100 by placing a new sample contained in a cell sample vessel 46 into the tube lifter 48 and the RUN switch 64 is actuated by the operator. In step 102, the tube lifter up (TLU) line 47 is energized causing the tube lifter 48 to be driven upward for 59 computer ticks (each second is equal to 18 seconds) or approximately 3 computer ticks. This completes the upward ascent of the tube lifter. The tube lifter is maintained in the up position by a retaining magnet. In step 104, while the tube lifter 48 is maintained in the up position, valve V2 54 is energized or opened for 18 computer ticks or one second to perform the auto-boost function wherein the cell sample is aspirated from the cell sample vessel 46 at 5 to 7 times the normal rate to boost the cell sample flow rate through the analysis region 30 to the normal test level more rapidly. In step 106, valve V1 52 is energized for 126 computer ticks or 7 seconds, while the tube lifter is maintained in its upward position and V2 54 remains open. After this, data acquisition begins in step 108 for whatever period is necessary for the particular test being run while V1 52 and V2 54 remain energized and the tube lifter 48 is maintained in its up position. The data acquisition period of step 108 includes a period for the system to reach full stabilization of the sheath and sample flows, for example seven seconds.

Data acquisition is terminated, either by computer control or by the operator pressing the STOP operator access switch 66 in step 110 of FIG. 3B. In step 12, valves V1 52 and V2 54 are each maintained in the energized or open position, the tube lifter 48 is maintained in its upward position while the reverse flush pump 76 is energized to perform the reverse flush cycle for 36 computer ticks or 2 seconds. In step 114, for the next 2 computer ticks or just 0.1 seconds, while valves V1 52 and V2 54 are still energized or open, the tube lifter down line 49 is energized to begin the descent of the tube lifter 48. The tube lifter down (TLD) line causes the tube lifter 48 to be driven downward. In step 116, the tube lifter down line 49 is deenergized while valves V1 52 and V2 54 are still maintained in an energized or open condition for 54 computer ticks or 3 seconds. During this time, the tube lifter 48 continues a slow descent begun in the previous step 14 in which the tube lifter line 48 was energized for just 0.1 second. The slow descent of the tube lifter 48 allows the cell sample vessel 46 to slowly separate from the cell sample uptake tube 44 and the residual cell sample to drain from the cell sample uptake tube 44 back into the descending cell sample vessel 46. Finally, in step 118, valves V1 52 and V2 54 are deenergized or closed while valve V3 56, the atmospheric inlet valve, is energized or opened and the tube lifter down line 49 is energized for 54 computer ticks or 3 seconds driving the tube lifter 48 downward. The tube lifter 48 stops automatically and valve V3 56 is deenergized as the cycle terminates. This sequence of events is also depicted in the computer control timing diagram of FIG. 4.

Figure 5:
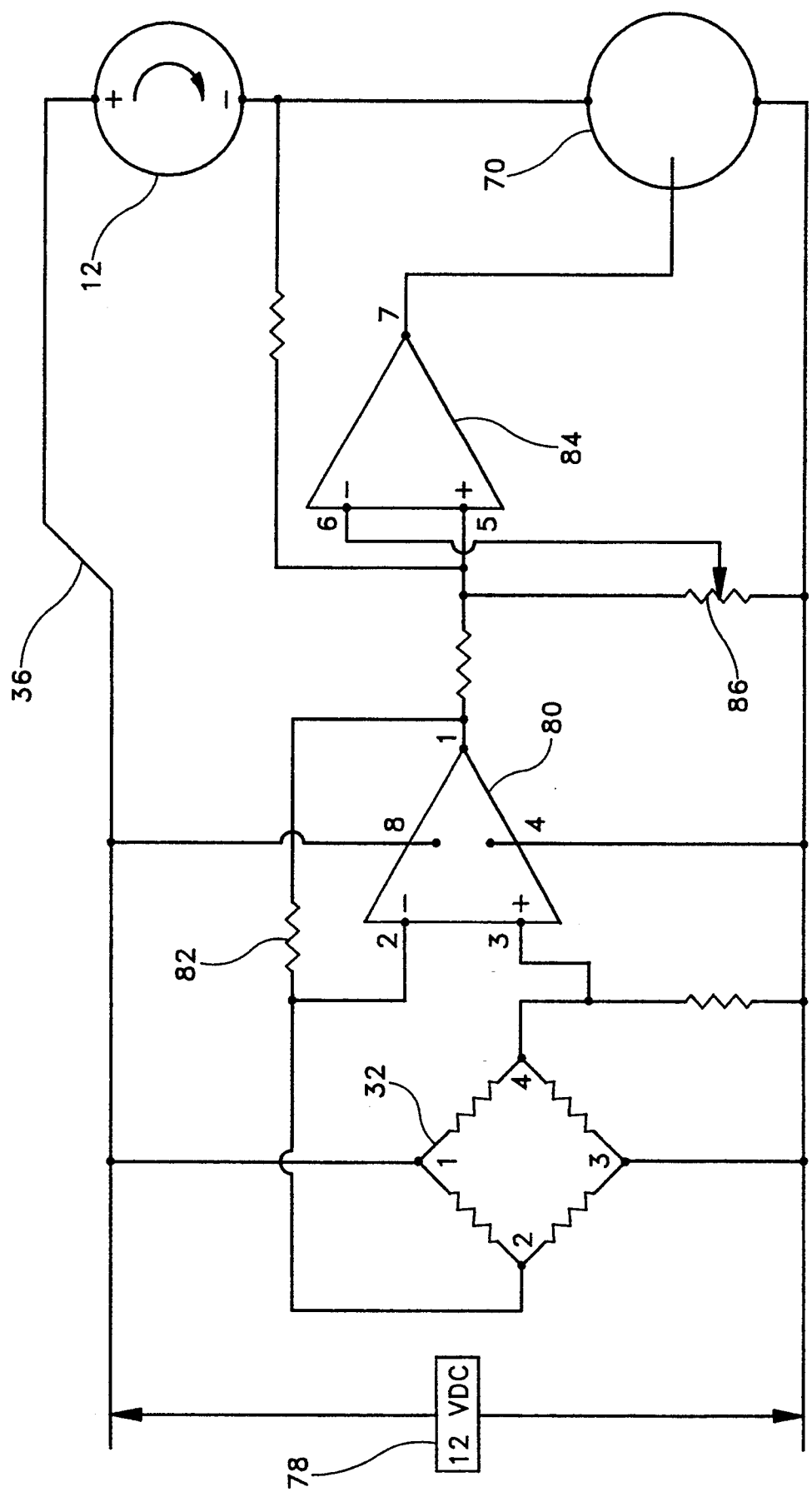
FIG. 5 is a circuit diagram depicting the closed loop control for the vacuum pump and discharge pressure switch.

The solid state control circuit for the vacuum pump is depicted in FIG. 5. Operational amplifier 80 accepts input signals from vacuum sensor 32, connected to the inlet of pulsation damper 34. Vacuum sensor 32 monitors the over-all system vacuum or pressure level. The vacuum sensor 32 incorporates a diaphragm of a piezoresistive material which generates a proportional voltage when deflected in response to the system pressure or vacuum level. The output from vacuum sensor 32 is modeled in the form of a Wheatstone Bridge which is energized at terminals 1 and 3 from a 12 V power source 78. The Wheatstone bridge is picked up on balance from terminals 2 and 4 and applied to the terminals of operational amplifier 80, which has a feedback resistor 82 of 100K Ohms. The output of operational amplifier 82 at pin 1 is a voltage which has a proportional linear relationship to the system pressure or vacuum level (voltage/pressure). The output of the operational amplifier 80 is applied to the positive input terminal of operational amplifier 84. Potentiometer 86 ranges from a positive 12 V setting to a zero voltage setting and acts as the vacuum setting level control which is applied to the negative input terminal of operational amplifier 84. Operational amplifier 84 acts as a comparator to determine which input voltage is greater.

If the vacuum level is inadequate, the current from operational amplifier 84 drives motor driver 70 (Power MOSFET), to output more current to the motor of vacuum pump 12 to drive it faster and harder in an effort to bring the system vacuum level up to the data level set by the potentiometer 86. This scheme provides utilization of the full drive voltage (to within a few tenths of a volt) from the motor of vacuum pump 12. The "no load" to "full load" ratio provide has been found to be within approximately 3% of the vacuum setting. The vacuum level is set to approximately 4.5 psi vacuum below atmospheric pressure at the factory.

The discharge pressure switch 36 is normally closed. If there is no pressure at the discharge of the vacuum pump 12 then discharge pressure switch 36 remains closed and the vacuum pump control circuit functions normally. If excessive pressure builds up at the discharge conduit of the vacuum pump 12, then discharge pressure switch 36 opens the circuit, disconnecting power from the vacuum pump 12. Such an excessive pressure condition may occur when then the waste reservoir 18 is removed. In this event, quick disconnect device 38 seals off the conduit so that the system begins to output effluent into a dead-end passage thereby building up pressure. Provision of discharge pressure switch 36 prevents the motor of vacuum pump 12 from burning out or from spraying effluent saline solution into the environment.

Vacuum sensor 32 may be provided by Motorola Vacuum Sensor Model MPX2051. Motor driver 70 is provided, for example, by Power MOSFET Model 1RF513. One advantage of regulating power delivery to the motor of vacuum pump 12 based on a preselected system vacuum level is that the vacuum pump 12 runs only when required as a "demand" component. Thus, the vacuum pump 12 need not run at all during instrument STANDBY mode when no sheath fluid flows and may run only a few percent of the rated speed during normal test RUN mode thereby extending the life of the vacuum pump 12. The identical pump model is utilized as both the vacuum pump 12 and the pressure pump 76. This pump may be provided, for example by KNF Neuberger, Model NF30KVDC. The selection of this pump is based on the fact that it is self priming. When the system is first energized, the pump must be able to pull air through the system conduits followed some seconds later by pulling liquid to create the normal vacuum cycle. To perform this function, the vacuum pump must be "self-priming." In addition, when the pump is used as pressure pump 76, it must be able to flow the sheath fluid when in a non-energized state and must thus have a low pressure drop. The aforementioned model pump has very small pressure drop check valves which allow the fluid to be pulled through the pump without a great pressure drop.

What is claimed is:

1. A flow cytometer control system for controlling the delivery of a cell sample drawn from a vessel, comprising:
    a flow cell, in communication with a cell sample vessel, for performing cell sample analysis;
    an intake passage, connected to said flow cell, providing an ingress communication path for sheath fluid into said flow cell;
    first outlet passage, connected to said flow cell, providing a first egress communication path for said sheath fluid out of said flow cell;
    a vacuum pump with motor means, in vacuum communication with said first outlet passage and a second outlet passage, for pulling said sheath fluid through said flow cell;
    flow resistor means, connected to said intake passage, for developing a pressure drop along said intake passage to cause cell sample to be aspirated from said vessel into said flow cell;
    a first valve, connected to said intake passage, for controlling the flow of said sheath fluid into said flow cell at a predetermined cell sample flow rate;
    a second valve, connected to said first outlet passage, for controlling the flow of said sheath fluid out of said flow cell;
    control means for opening said second valve for a predetermined time prior to opening said first valve in order to permit a vacuum to be developed in said flow cell before opening said first valve thereby pulling cell sample through said flow cell to increase sample flow into said analysis region; and
    said control means being operatively connected to said first and second valves.

2. The control system of claim 1, further comprising:
    processor means, connected to said first and second valves, for controlling the actuation of said first and second valves under programmed control.

3. The control system of claim 1 further comprising:
    a sensor, connected to said first outlet passage, for sensing the vacuum level of said sheath fluid;
    driver means, coupled to said vacuum pump motor, for regulation of power delivery to said vacuum pump motor; and
    controller means, coupled to said sensor and said driver means, for controlling the operation of said driver based on said vacuum level;
    whereby power delivery to said vacuum pump motor may be modulated based on said vacuum level to adjust said vacuum level to a predetermined fixed value.

4. The control system of claim 1, further comprising:
    a supply reservoir connected to said first intake passage; and
    a waste reservoir connected to said first and second outlet passages.

5. The control system of claim 1, wherein said first and second valves are solenoid actuated.

6. The control system of claim 1, further comprising:
    a sensor, connected to said first outlet passage, for sensing the vacuum level of said sheath fluid;
    a driver, coupled to said vacuum pump motor, for regulation of power delivery to said vacuum pump motor; and
    controller means, coupled to said sensor and said driver, for controlling the operation of said driver based on said vacuum level;
    whereby power delivery to said vacuum pump motor is modulated based on said vacuum level thereby adjusting said vacuum level to a predetermined fixed value.

7. The control system of claim 1, further comprising:
    a sample uptake tube, connected to said flow cell, for providing a communication path into said flow cell; and
    a tube lifter, movably positioned a predetermined distance from said uptake tube, for moving said cell sample vessel to position said sample uptake tube inside said cell sample vessel, with the rate of descent of said tube lifter being controlled by a processor means;
    whereby any external residue in said sample uptake tube is allowed to drain into said cell sample vessel to reduce carryover of cell sample between test cycles.

8. The control system of claim 7, further comprising:
    a third valve, connected to said first outlet passage and to the atmosphere, for providing a communication path to atmospheric pressure at such time that said tube lifter is descending to substantially eliminate the vacuum developed in said flow cell thereby preventing air from being drawn into said flow cell with no sample being present.

9. The control system of claim 1, further comprising:
    a deaerator, connected to said intake passage, for removing gas dissolved in said sheath fluid.

10. The control system of claim 9, wherein sad deaerator is made of a material which is permeable to oxygen and nitrogen to allow these gases to diffuse through its wall when subjected to a vacuum.

11. The control system of claim 10, wherein said deaerator includes at least one length of tubing, and said tubing is contained within a jar which is subjected to said vacuum thereby serving to dampen the vacuum pulsations of said vacuum.

* * * * *